(12) United States Patent
Lee et al.

(10) Patent No.: US 10,067,104 B2
(45) Date of Patent: Sep. 4, 2018

(54) METHOD FOR PREPARING HYDROGEL BEAD FOR DETECTION OF HYDROFLUORIC ACID AND KIT COMPRISING THE SAME

(71) Applicant: INDUSTRY-ACADEMIC COOPERATION FOUNDATION YONSEI UNIVERSITY, Seoul (KR)

(72) Inventors: Sang Yup Lee, Seoul (KR); Chaemyeong Lee, Gwangju (KR); Min Chul Kim, Siheung-si (KR); Jin Young Kwak, Seoul (KR); Sang Woo Park, Daejeon (KR); Young Jun Lim, Seoul (KR); Chang Joon Keum, Yeongju-si (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 394 days.

(21) Appl. No.: 14/693,346

(22) Filed: Apr. 22, 2015

(65) Prior Publication Data
US 2016/0146739 A1    May 26, 2016

(30) Foreign Application Priority Data

Nov. 25, 2014 (KR) .................. 10-2014-0165327

(51) Int. Cl.
*G01N 21/78* (2006.01)
*G01N 31/22* (2006.01)

(52) U.S. Cl.
CPC .................. *G01N 31/22* (2013.01)

(58) Field of Classification Search
CPC ...................................... G01N 31/22
(Continued)

(56) References Cited

FOREIGN PATENT DOCUMENTS

| JP | 2005-156323 A | 6/2005 |
|----|---------------|--------|
| JP | 2005156323 | * 6/2005 |

(Continued)

OTHER PUBLICATIONS

Dai, Ya-Ni et al. (2008). "A Novel pH Sensitive N-Succinyl Chitosan/ALginate Hydrogel Bead for Nifedipine Delivery." Biopharm & Drug Dispos. 29: 173-184.*

(Continued)

*Primary Examiner* — Jill A Warden
*Assistant Examiner* — Jacqueline Brazin
(74) *Attorney, Agent, or Firm* — LRK Patent Law Firm

(57) ABSTRACT

The present invention relates to a hydrogel bead for detecting hydrofluoric acid and a kit comprising the same, and more particularly, to a hydrogel bead capable of detecting hydrofluoric acid using an organometallic ligand compound that reversibly changes color depending on the concentration of hydrofluoric acid when coming into contact with hydrofluoric acid, and to a kit for detecting hydrofluoric acid comprising the same. In an embodiment, a method for preparing a hydrogel bead for detecting hydrofluoric acid comprises the steps of: mixing an organic compound, which contains an aromatic functional group having at least one hydroxyl group bonded thereto, with a solution of a metal-ligand compound that bonds with the organic compound, thereby preparing a mixed solution; dropping the mixed solution onto a gelling agent; and adding coagulating agent to the mixture resulting from the dropping step to form a porous bead.

2 Claims, 6 Drawing Sheets
(6 of 6 Drawing Sheet(s) Filed in Color)

(a)

(b)

(58) Field of Classification Search
USPC .......................................................... 422/430
See application file for complete search history.

(56) References Cited

FOREIGN PATENT DOCUMENTS

| | | |
|---|---|---|
| JP | 2009-186479 A | 8/2009 |
| KR | 10-2009-0067862 A | 6/2009 |

OTHER PUBLICATIONS

Ivanov, V. (2006). "Pyrocatechol Violet in spectrophotometric and novel optical methods." Ru. Chem. Rev. 75(3). 283-296. (Year: 2006).*

Ya-Ni Dai et al., "A Novel pH Sensitive N-Succinyl Chitosan/Alginate Hydrogel Bead for Nifedipine Delivery", Biopharmaceutics & Drug Disposition 29: 173-184, 2008, Wiley InterScience.

Yoo Kyung Lee et al., "Pyrocatechol violet (PCV) gel-based pH sensor", Abstracts Presented at the 48th KSIEC Meeting, Nov. 2013, Deajeon Convention Center, South Korea.

* cited by examiner

METHOD FOR PREPARING HYDROGEL BEAD FOR DETECTION OF HYDROFLUORIC ACID AND KIT COMPRISING THE SAME

BACKGROUND OF THE INVENTION

Field of the Invention

The present invention relates to a hydrogel bead for detecting hydrofluoric acid and a kit comprising the same. More particularly, the present invention relates to a hydrogel bead capable of detecting hydrofluoric acid using an organometallic ligand compound that reversibly changes color depending on the concentration of hydrofluoric acid when coming into contact with hydrofluoric acid, and to a kit for detecting hydrofluoric acid comprising the same.

Description of the Prior Art

Hydrofluoric acid is classified as a weak acid, because it is not easily ionized due to a strong hydrogen bond between fluorine and hydrogen, unlike hydrochloric acid that is classified as a strong acid, or other hydrogen halides such as hydrogen bromide. However, if the concentration of hydrofluoric acid in any material increases, the acidity increases rapidly, and thus the material is classified as a highly toxic material, and emits mist odor with an irritant odor.

Hydrofluoric acid is highly useful in various industrial fields, and is mainly used as an alternative to Flon or a raw material for producing fluorocarbon resin. Because hydrofluoric acid easily melts glass or metals, it is used to process the surface of glass or as an agent for treating the surface of a titanium golf club head, the surface of a pot, or the surface of a semiconductor in semiconductor manufacturing processes. In addition, hydrofluoric acid is used as a catalyst in the production of high-quality gasoline having high octane number, and is also widely used for the synthesis of fluorinated organic compounds.

Although hydrofluoric acid is highly useful in various industrial fields as described above, hydrofluoric acid solution and hydrofluoric acid gas are acute and contagious toxic materials that can be used as chemical warfare. Particularly, these materials have a serious problem in that they are easily absorbed into the human body. Because the size of fluorine ions ($F^-$) is smaller than the size of other halogen ions ($Cl^-$, $Br^-$, $I^-$, etc.), hydrofluoric acid easily penetrates the skin. In addition, halogen ions other than fluorine ions are completely dissociated in an aqueous solution by their bonding with hydrogen ions, hydrofluoric acid is not completely dissociated, and thus when it penetrates the skin, hydrofluoric molecules are mostly absorbed into the skin tissue. The extent to which hydrofluoric acid is dissociated into cations ($H^+$) and anions ($F^-$) varies depending on the concentration thereof, and even non-dissociated hydrofluoric acid molecules can be easily absorbed into the skin, because the size thereof is small.

Dissociated fluorine ions in the body react with calcium ions ($Ca^{2+}$) or magnesium ions ($Mg^{2+}$) to form the insoluble compound calcium fluoride ($CaF_2$) or magnesium fluoride ($MgF_2$), and for this reason, the body's electrolyte balance is broken while the calcium ion and magnesium ion concentrations of the electrolyte become lower than the normal concentrations.

Particularly, calcium ions play an important role in signaling in vivo, and when hydrofluoric acid enters the body to extremely reduce the concentration of calcium ions, respiratory muscle becomes hardened, resulting in death by suffocation. In addition, if fluorine ions react with bone, they will damage the bone, and fine powdery particles will be deposited due to the produced calcium fluoride. Meanwhile, if hydrofluoric acid aerosol comes into contact with a plant, it will be absorbed into the tissue of the plant to make the metabolism of the plant difficult, the leaf will turn yellow, and ultimately the plant will wither.

Accordingly, to secure safety in processes in which hydrofluoric acid is used, methods for detecting hydrofluoric acid have been actively studied. For example, Korean Patent Laid-Open Publication No. 2009-0067862 (published on Jun. 25, 2009) discloses an analysis kit that can selectively analyze the concentration of free hydrofluoric acid in a mixture of hydrofluoric acid with other acid or solution. The analysis kit is a disposable kit that detects hydrofluoric acid by spectrophotometrically analyzing a color change that occurs when a hydrofluoric acid component comes into contact with a mixture solution containing an iron solution, a nitric acid medium and an acetylacetone solution.

In addition, Japanese Patent Laid-Open Publication No. 2005-156323 (published on Jun. 16, 2005) discloses a method for detecting hydrofluoric acid, which comprises adding an aqueous solution sample containing hydrofluoric acid to an aqueous solution containing a polynuclear complex composed of zirconium, pyrocatechol violet and a polydentate ligand, and analyzing the resulting color change.

However, the kit for detecting hydrofluoric acid according to the prior art is expensive, and is in a liquid form that is not easy to store and transport and not convenient to carry.

PRIOR ART DOCUMENTS

Patent Documents

Patent Document 1: Korean Patent Laid-Open Publication No. 2009-0067862 (published on Jun. 25, 2009);
Patent Document 2: Japanese Patent Laid-Open Publication No. 2005-156323 (published on Jun. 16, 2005).

SUMMARY OF THE INVENTION

The present invention relates to a hydrogel bead for detecting hydrofluoric acid and a kit comprising the same, and more particularly, to a hydrogel bead for detecting hydrofluoric acid, which comprises a porous bead impregnated with an organometallic ligand compound that changes color depending on the concentration of hydrofluoric acid when coming into contact with hydrofluoric acid, and to a kit for detecting hydrofluoric acid comprising the hydrogel bead.

The present invention has been made in order to solve the above-mentioned problems occurring in the prior art, and it is an object of the present invention to provide a hydrogel bead for detecting hydrofluoric acid, which is relatively inexpensive, clearly changes color depending on the concentration of hydrofluoric acid, and is easy to carry, and a kit comprising the hydrogel bead.

To achieve the above object, in accordance with one embodiment of the present invention, there is provided a method for detecting hydrofluoric acid, comprising the steps of: mixing an organic compound, which contains an aromatic functional group having at least one hydroxyl group bonded thereto, with a solution of a metal-ligand compound that bonds with the organic compound; bringing hydrofluoric acid into contact with the mixed solution prepared in the mixing step; observing a change in color of the mixed solution, which occurs after contact with the hydrofluoric acid.

In accordance with another embodiment of the present invention, there is provided a method for preparing a hydrogel for detecting hydrofluoric acid, the method comprising the steps of: mixing an organic compound, which contains an aromatic functional group having at least one hydroxyl group bonded thereto, with a solution of a metal-ligand compound that bonds with the organic compound; and dropping the mixed W solution of the mixing step onto a gelling agent.

In accordance with still another embodiment of the present invention, there is provided a method for preparing a hydrogel bead for detecting hydrofluoric acid, the method comprising the steps of: mixing an organic compound, which contains an aromatic functional group having at least one hydroxyl group bonded thereto, with a solution of a metal-ligand compound that bonds with the organic compound, thereby preparing a mixed solution; dropping the mixed solution onto a gelling agent; and adding coagulating agent to the mixture resulting from the dropping step to form a porous bead.

In accordance with still another embodiment of the present invention, there is provided a method for preparing a hydrogel bead for detecting hydrofluoric acid, the method comprising the steps of: mixing a gelling agent with a coagulating agent to prepare a porous bead; mixing an organic compound, which contains an aromatic functional group having at least one hydroxyl group bonded thereto, with a solution of a metal-ligand compound that bonds with the organic compound, thereby preparing a mixed solution; and impregnating the mixed solution into the porous bead.

In the present invention, the organic compound may comprise a compound represented by the following formula 1:

Formula 1 wherein $R^1$ and $R^2$ may be the same or different and are each a cyclic group having 4 to 10 carbon atoms, and $R^3$ is selected from the group consisting of a hydroxyl group, a nitrile group and hydrogen. Preferably, the organic compound may be pyrocatechol violet.

The metal-ligand compound may be represented by the following formula 2:

Formula 2 wherein M is a metal ion selected from the group consisting of titanium (Ti), zirconium (Zr), hafnium (Hf), vanadium (V), chromium (Cr), molybdenum (Mo), tungsten (W), copper (Cu) and silver (Ag); $X^1$ to $X^4$ are each independently selected from the group consisting of oxygen, nitrogen and carbon atoms; L1 and L2 are each an atom group forming a bidentate ligand; Sol is a solution that is capable of coordinating to metal ions and contains one selected from the group consisting of a hydroxyl-containing group, an amine-containing group, an amide-containing group, and combinations thereof, and/or water.

The gelling agent may be at least one selected from the group consisting of alginate, natural gum, gelatin, pectin, arabinogalactan, agar, carrageenan, furcellaran and modified starch.

The coagulating agent may be at least one selected from the group consisting of potassium chloride, sodium chloride, magnesium chloride, and calcium chloride.

In accordance with still another embodiment of the present invention, there is provided a kit for detecting hydrofluoric acid, comprising: a plate-type support; a transparent body disposed on the support and made of a material selected from the group consisting of glass, quartz and plastic; a sensor unit received in a portion of the body; and an external communication unit connected to the top of the body, wherein a hydrogel bead for detecting hydrofluoric acid is placed in the sensor unit so that it will change color in response to hydrofluoric acid introduced through the external communication unit.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Hereinafter, embodiments of the present invention will be described with reference to the accompanying drawings. However, these embodiments are merely exemplary embodiments of the present invention and do not represent all the technical ideas of the present invention. Thus, it shall be understood that various equivalents and modified embodiments which may replace these embodiments at the filing date of the present application can exist.

A method for detecting hydrofluoric acid according to one embodiment of the present invention comprises the steps of:

mixing an organic compound, which contains an aromatic functional group having at least one hydroxyl group bonded thereto, with a solution of a metal-ligand compound that bonds with the organic compound; bringing hydrofluoric acid into contact with the mixed solution prepared in the mixing step; observing a change in color of the mixed solution, which occurs after contact with the hydrofluoric acid.

In the detection method, the organic compound may comprise a compound represented by the following formula 1:

Formula 1 wherein $R^1$ and $R^2$ may be the same or different and are each a cyclic group having 4 to 10 carbon atoms, and $R^3$ is selected from the group consisting of a hydroxyl group, a nitrile group and hydrogen. Preferably, the organic compound may be pyrocatechol violet. Preferably, the organic compound may be an organic indicator such as pyrocatechol violet, bromocresol green, bromophenol blue or cresol red. More preferably, the organic compound may be pyrocatechol violet that reacts with various metal ions through the catechol group that is a chemical functional group.

The metal-ligand compound may be represented by the following formula 2:

Formula 2 wherein M is a metal ion selected from the group consisting of titanium (Ti), zirconium (Zr), hafnium (Hf), vanadium (V), chromium (Cr), molybdenum (Mo), tungsten (W), copper (Cu) and silver (Ag); $X^1$ to $X^4$ are each independently selected from the group consisting of oxygen, nitrogen and carbon atoms; L1 and L2 are each an atom group forming a bidentate ligand; Sol is a solution that is capable of coordinating to metal ions and contains one selected from the group consisting of a hydroxyl-containing group, an amine-containing group, an amide-containing group, and combinations thereof, and/or water. Preferably, the metal ion is titanium, and the metal-ligand compound is TBLADH.

In the mixing step, regarding the mixing ratio between pyrocatechol violet and TBLADH, 100-500 µl of 0.003 mM TBLADH is preferably mixed with 10 µl of 1 mM pyrocatechol violet. If TBLADH is mixed in an amount of less than 100 µl, the binding reaction of TBLADH will be insufficient, and if TBLADH is mixed in an amount of more than 500 µl, the amount of TBLADH that does not react will increase, resulting in disadvantages in economic terms.

A method for preparing a hydrogel for detecting hydrofluoric acid according to another embodiment of the present invention comprises preparing a hydrogel by dropping the mixed solution onto a gelling agent. More specifically, the preparation method comprises the steps of mixing an organic compound, which contains an aromatic functional group having at least one hydroxyl group bonded thereto, with a solution of a metal-ligand compound that bonds with the organic compound; and dropping the mixed solution of the mixing step onto a gelling agent.

A method for preparing a hydrogel bead for detecting hydrofluoric acid according to still another embodiment of the present invention comprises preparing a porous bead and impregnating the mixed solution into the bead. More specifically, the preparation method comprises the steps of: mixing a gelling agent with a coagulating agent to prepare a porous bead; mixing an organic compound, which contains an aromatic functional group having at least one hydroxyl group bonded thereto, with a solution of a metal-ligand compound that bonds with the organic compound, thereby preparing a mixed solution; and impregnating the mixed solution into the porous bead.

A method for preparing a hydrogel bead for detecting hydrofluoric acid according to yet another embodiment of the present invention comprises preparing a bead by adding a coagulating agent to the hydrogel prepared as described above. More specifically, the preparation method comprises the steps of mixing an organic compound, which contains an aromatic functional group having at least one hydroxyl group bonded thereto, with a solution of a metal-ligand compound that bonds with the organic compound, thereby preparing a mixed solution, dropping the mixed solution onto a gelling agent; and adding coagulating agent to the mixture resulting from the dropping step to form a porous bead.

The gelling agent may be at least one selected from the group consisting of alginate, natural gum, gelatin, pectin, arabinogalactan, agar, carrageenan, furcellaran and modified starch. Preferably, it is alginate.

Figure 1:
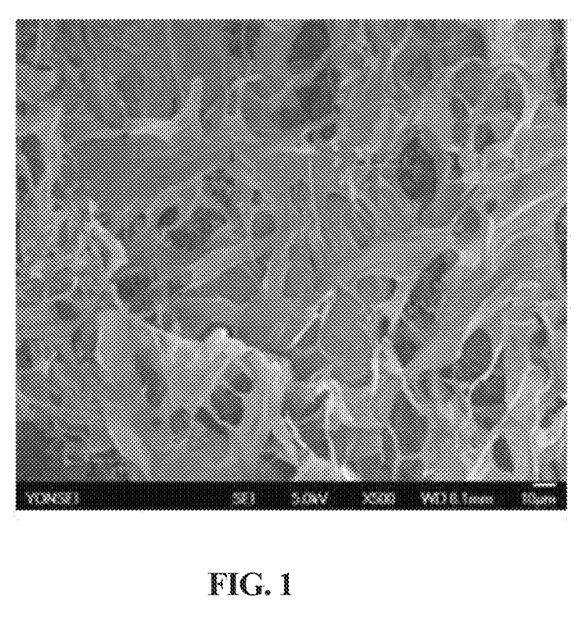
FIG. 1 is an SEM image showing a porous alginate gel.
Figure 2:
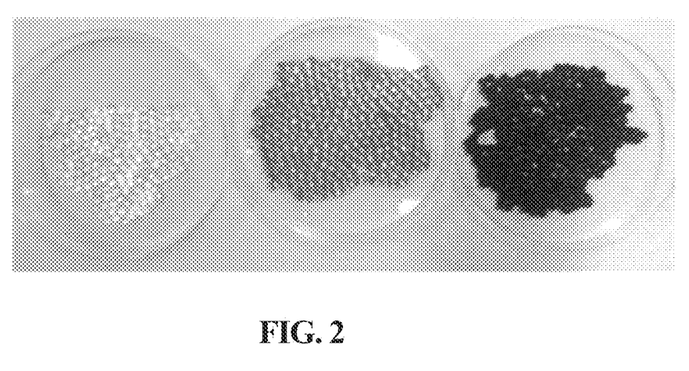
FIG. 2 is an image showing a hydrogel bead (left), a hydrogel bead impregnated with pyrocatechol violet (middle), and a hydrogel impregnated with pyrocatechol violet and titanium (IV) bis(ammonium lactato)dihydroxide solution (hereinafter referred to as TBLADH) (right).
Figure 3:
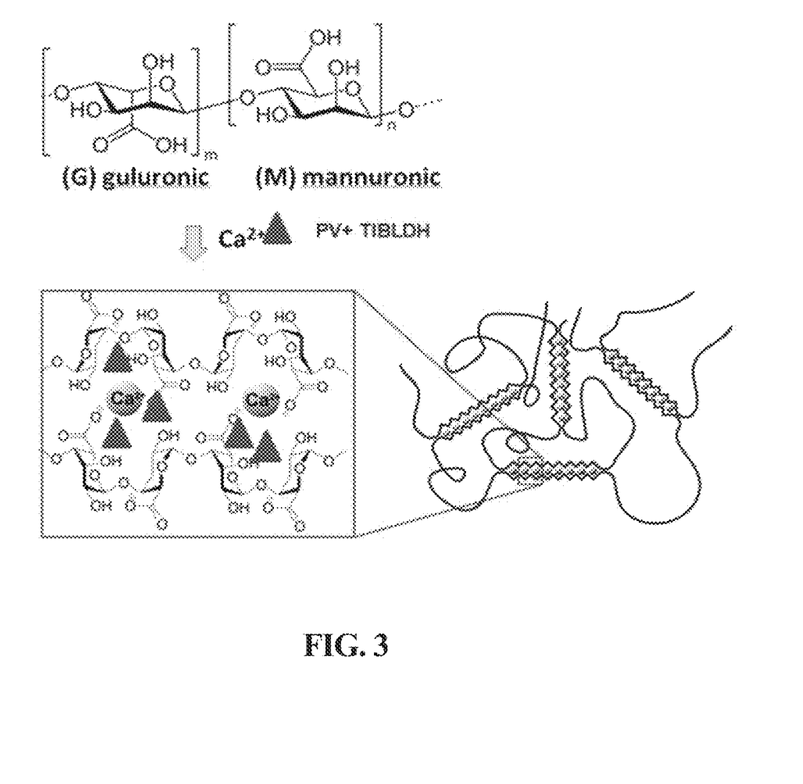
FIG. 3 is a schematic view showing pyrocatechol violet mixed with TBALDH in calcium-alginate.

An alginate polymer having a large amount of carboxyl groups has a network structure as shown in FIG. 1, and is composed of mannuronic acid and its structural isomer guluronic acid. If alginate is prepared in the form of a porous gel, a dye solution can be penetrated into the porous gel by a capillary effect, and the porous gel can be prepared into beads as shown in FIG. 2 by using monovalent or divalent cations as a coagulating agent, because it easily reacts with the monovalent or divalent cations. The coagulating agent may be at least one selected from the group consisting of potassium chloride, sodium chloride, magnesium chloride, and calcium chloride. Preferably, the coagulating agent is calcium chloride. As shown in FIG. 2, pure hydrogel beads are transparent, and hydrogel beads containing pyrocatechol violet are yellow in color, and hydrogel beads containing both pyrocatechol violet and TBLADH are dark violet in color. Herein, pyrocatechol violet is an indicator that easily reacts with metal ions, and changes color after its binding to TBLADH. FIG. 3 shows the structure of the hydrogel bead impregnated with pyrocatechol violet and TBLADH.

In the dropping step, the mixed solution of pyrocatechol violet and TBLADH and the gelling agent alginate are mixed at a volume ratio of 1:1. If the mixed solution is added at a ratio lower than the above range, the change in color of the hydrogel bead upon contact with hydrofluoric acid will be insignificant, and if the mixed solution is added at a ratio higher than the above range, a portion of the mixed solution will not be impregnated into the gelling agent.

A kit for detecting hydrofluoric acid according to still another embodiment of the present invention comprises: a plate-type support; a transparent body disposed on the support and made of a material selected from the group consisting of glass, quartz and plastic; a sensor unit received in a portion of the body; and an external communication unit connected to the top of the body, wherein a hydrogel bead for detecting hydrofluoric acid is placed in the sensor unit so that it will change color response to hydrofluoric acid introduced through the external communication unit.

More specifically, the hydrogel bead is dark violet in color, and if it comes into contact with hydrofluoric acid, TBLADH will bond with hydrofluoric acid through a strong hydrogen bond while the original bond between TBLADH and pyrocatechol violet will be broken, and thus the hydrogel will show a yellow color that is the natural color of pyrocatechol violet. Based on this change in color, hydrofluoric acid can be detected.

Hereinafter, examples of the present invention will be described with reference to the accompanying drawings. However, these examples are merely exemplary examples of the present invention and do not represent all the technical ideas of the present invention. Thus, it shall be understood that various equivalents and modified examples which may replace these examples at the filing date of the present application can exist.

Figure 4:
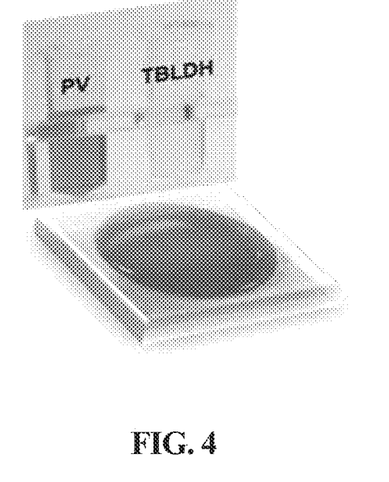
FIG. 4 is an image showing a mixed solution of pyrocatechol violet and TBALDH, prepared in Example 1 of the Present invention.

Example 1: Preparation of Organometallic Ligand Compound for Detection of Fluoric Acid To prepare an organometallic ligand compound for detection of hydrofluoric acid, 10 ml of 1 mM pyrocatechol violet solution was mixed with 200 µl of 0.003 mM TBLADH to make a mixed solution as shown in FIG. 4.

Example 2: Preparation of Hydrogel Bead for Detection of Hydrofluoric Acid

Figure 5:
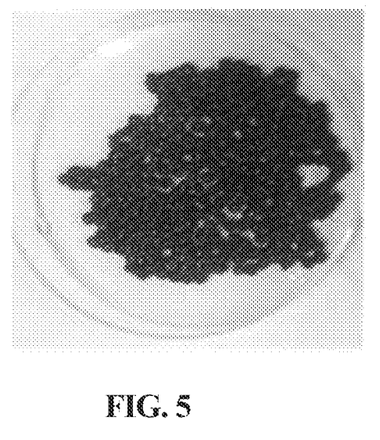
FIG. 5 is an image showing a hydrogel bead for detecting hydrofluoric acid, prepared in Example 2 of the present invention.

To prepare a hydrogel bead for detection of hydrofluoric acid, alginate (Mw 25,000) was dissolved in distilled water at a concentration of 1% (w/v) to make an aqueous alginate solution. The aqueous alginate solution and the mixed solution prepared in Example 1 were mixed with each other at a volume ratio of 1:1, and then immersed in 1M calcium chloride, thereby forming a bead as shown in FIG. 5.

Example 3: Observation of Change in Color of Hydrogel Bead in Solutions of Hydrofluoric Acid and Various Acids In order to evaluate the selective response of the hydrogel bead of Example 2 to hydrofluoric acid, the responses of the hydrogel bead to various acid solutions were evaluated under the same conditions in the following manner.

Figure 6:
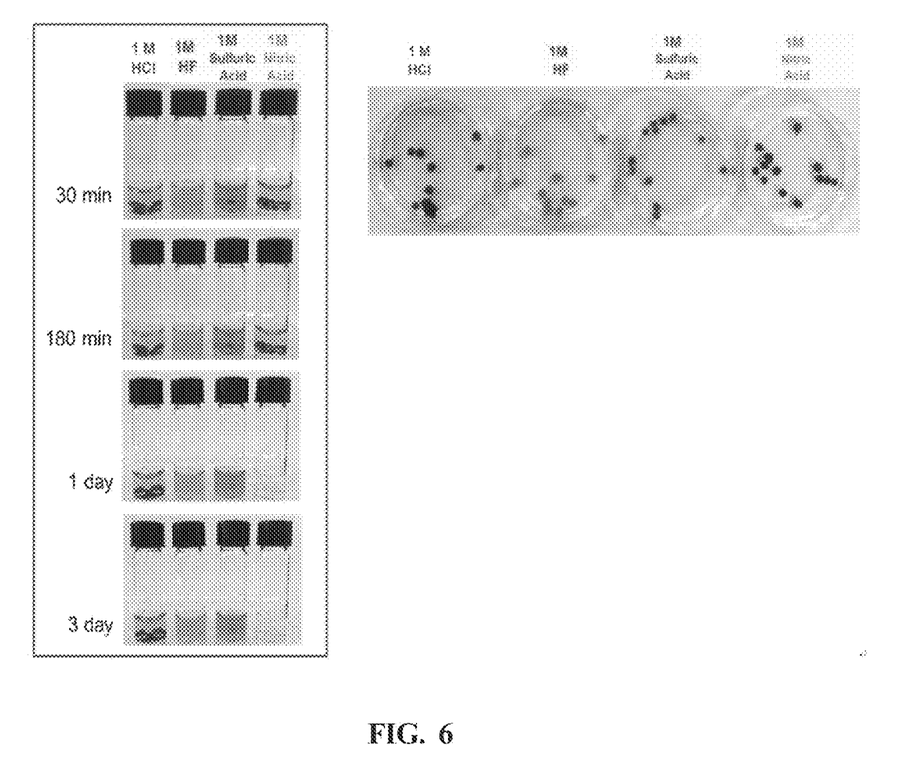
FIG. 6 is an image showing the changes in color of a hydrogel beads in solutions of hydrofluoric acid and various acids, observed in Example 3 of the present invention.

The hydrogel bead was immersed in each of 1M hydrofluoric acid, hydrochloric acid, sulfuric acid and nitric acid, and then observed for 30 minutes, 180 minutes, 1 day and 3 days. The results of the observation are shown in FIG. 6. As can be seen in FIG. 6, the bead in hydrochloric acid changed color to yellow, unlike those in other acids. Also, the color of the bead in nitric acid gradually disappeared, unlike those in other acids. This is because when the bead comes into contact with nitric acid, TBLADH is separated by forming a hydrogen bond with nitric acid, and the natural structure of the remaining pyrocatechol violet is changed due to the strong acid to lose its color.

Example 4: Observation of Change in Color of Organometallic Ligand Compound Solution in Hydrofluoric Acid and Acetic Acid (Weak Acid)

Figure 7:
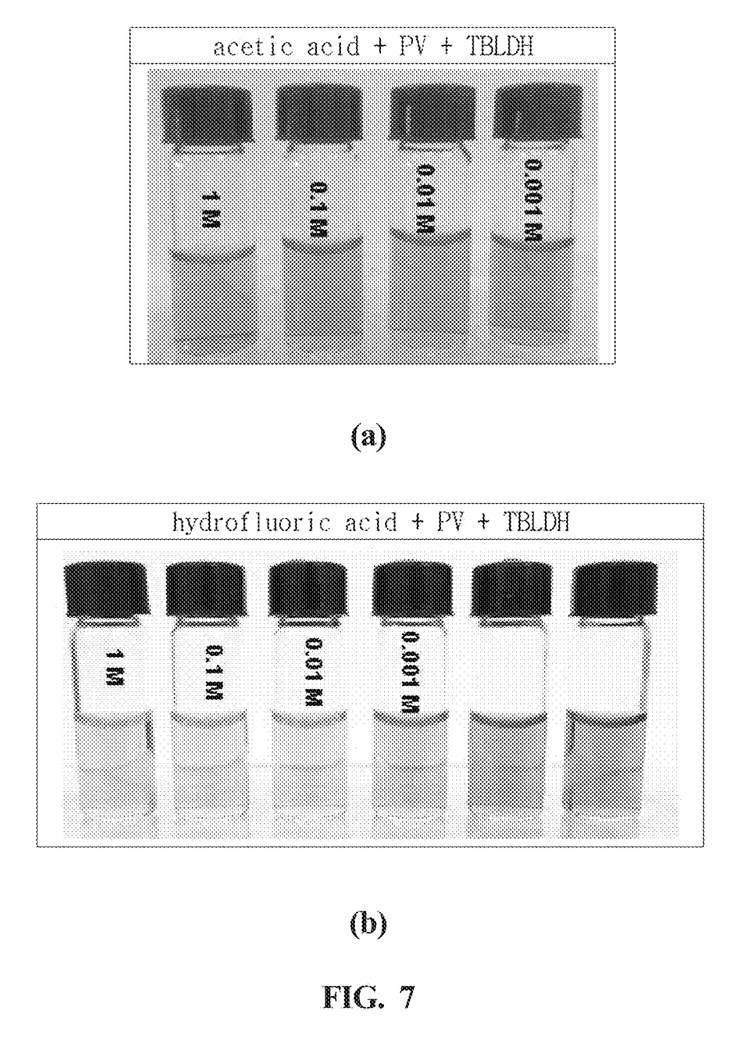
FIG. 7 is an image showing the change in color of a mixed solution of pyrocatechol violet and TBALDH with changes in the concentration of hydrofluoric acid and acetic acid, observed in Example 4 of the present invention.

In order to evaluate the selective response of the organometallic ligand compound of Example 1 to hydrofluoric acid, each of acetic acid (FIG. 7(a)) or hydrofluoric acid (FIG. 7(b)) and was added to the compound solution at a concentration ranging from 0.001 M to 1 M, and a change in the color of the compound solution was observed. The results of the observation are shown in FIGS. 7(a) and (b). As can be seen in FIGS. 7(a) and (b), the compound solution to which acetic acid was added did not significantly change color, whereas the compound solution to which hydrofluoric acid was added reversibly changed color depending on the concentration of hydrofluoric acid. Herein, the yellow color was more intense as the concentration of hydrofluoric acid increased, and when the concentration of hydrofluoric acid was 0.001 M or lower, no change in the color appeared.

Example 5: Observation of Change in Color of Hydrogel Bead in Hydrofluoric Acid and Acetic Acid (Weak Acid)

Figure 8:
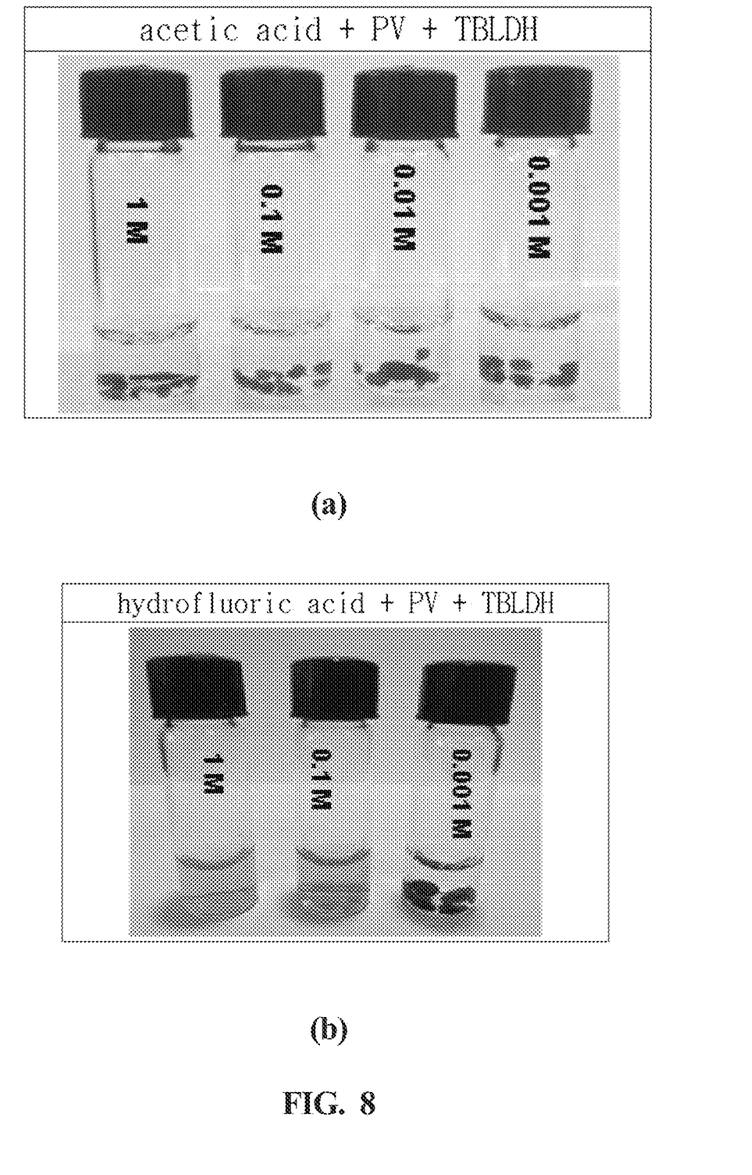
FIG. 8 is an image showing the changes in color of a hydrogel bead with changes in the concentrations of hydrofluoric acid and acetic acid, observed in Example 5 of the present invention.

In order to evaluate the selective response of the hydrogel bead of Example 2 to hydrofluoric acid, each of acetic acid (FIG. 8(a)) or hydrofluoric acid (FIG. 8(b)) was added to the hydrogel bead at a concentration ranging from 0.001 M to 1 M, and a change in the color of the compound solution was observed. The results of the observation are shown in FIG. 8. As can be seen in FIGS. 8(a) and (b), the hydrogel bead to which acetic acid was added did not significantly change color, whereas the hydrogel bead to which hydrofluoric acid was added reversibly changed color depending on the concentration of hydrofluoric acid. Herein, when the concentration of hydrofluoric acid was 0.001 M or lower, no change in the color appeared.

As described above, when the hydrogel bead for detecting hydrofluoric acid according to the present invention came into contact with hydrofluoric acid, it reversibly changed color from dark violet to yellow depending on the concentration of hydrofluoric acid, thereby detecting hydrofluoric acid. It was shown that the detectable minimum concentration of hydrofluoric acid was 0.001 M.

As described above, the hydrogel bead for detecting hydrofluoric acid according to the present invention and a kit comprising the same clearly change color when coming into contact with hydrochloric acid, and thus make it possible to visually detect hydrofluoric acid. Also, the kit of the present invention is inexpensive compared to conventional kits for detecting hydrofluoric acid. In addition, the hydrogel according to the present invention is easy to store and transport, can be prepared in a bead form and other various forms so as to maintain its inherent properties, and is convenient to carry.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method for preparing a hydrogel bead for detecting hydrofluoric acid, comprising the steps of:
   mixing an organic compound, which contains an aromatic functional group having at least one hydroxyl group bonded thereto, with a solution of a metal-ligand compound that bonds with the organic compound, thereby preparing a mixed solution;
   dropping the mixed solution onto a gelling agent; and
   adding coagulating agent to the mixture resulting from the dropping step to form a porous bead, wherein the organic compound comprises a compound represented by the following formula 1:

Formula 1 wherein $R^1$ and $R^2$ may be the same or different and are each a cyclic group having 4 to 10 carbon atoms, and $R^3$ is selected from the group consisting of a hydroxyl group, a nitrile group and hydrogen, wherein the metal-ligand compound is represented by the following formula 2:

Formula 2 wherein M is a titanium (Ti) ion; $X^1$ to $X^4$ are each independently selected from the group consisting of oxygen, nitrogen and carbon atoms; Li and L2 are each an atom group forming a bidentate ligand; Sol is a solution that is capable of coordinating to metal ions and contains one selected from the group consisting of a hydroxyl-containing group, an amine-containing group, an amide-containing group, and combinations thereof and/or water, wherein the coagulating agent is at least one selected from the group consisting of potassium chloride, sodium chloride, magnesium chloride, and calcium chloride, wherein the gelling agent is at least one selected from the group consisting of alginate, natural gum, gelatin, pectin, arabinogalactan, agar, carrageenan, furcellaran and modified starch, and wherein the organic compound is pyrocatechol violet.

2. A method for preparing a hydrogel bead for detecting hydrofluoric acid, comprising the steps of:

mixing a gelling agent with a coagulating agent to prepare a porous bead;

mixing an organic compound, which contains an aromatic functional group having at least one hydroxyl group bonded thereto, with a solution of a metal-ligand compound that bonds with the organic compound, thereby preparing a mixed solution; and impregnating the mixed solution into the porous bead, wherein the organic compound comprises a compound represented by the following formula 1:

Formula 1 wherein $R^1$ and $R^2$ may be the same or different and are each a cyclic group having 4 to 10 carbon atoms, and $R^3$ is selected from the group consisting of a hydroxyl group, a nitrile group and hydrogen, wherein the metal-ligand compound is represented by the following formula 2:

Formula 2 wherein M is a titanium (Ti) ion; $X^1$ to $X^4$ are each independently selected from the group consisting of oxygen, nitrogen and carbon atoms; L1 and L2 are each an atom group forming a bidentate ligand; Sol is a solution that is capable of coordinating to metal ions and contains one selected from the group consisting of a hydroxyl-containing group, an amine-containing group, an amide-containing group, and combinations thereof, and/or water, wherein the coagulating agent is at least one selected from the group consisting of potassium chloride, sodium chloride, magnesium chloride, and calcium chloride, wherein the gelling agent is at least one selected from the group consisting of alginate, natural gum, gelatin, pectin, arabinogalactan, agar, carrageenan, furcellaran and modified starch, and wherein the organic compound is pyrocatechol violet.

\* \* \* \* \*